United States Patent [19]

Kopineck et al.

[11] 4,377,746

[45] Mar. 22, 1983

[54] DEVICE FOR DETECTING SURFACE FLAWS OF RAPIDLY MOVING SHEET MATERIAL

[75] Inventors: H. J. Kopineck; Wilhelm Tappe, both of Dortmund, Fed. Rep. of Germany

[73] Assignee: Hoesch Werke Aktiengesellschaft, Dortmund, Fed. Rep. of Germany

[21] Appl. No.: 208,819

[22] Filed: Nov. 20, 1980

[30] Foreign Application Priority Data

Dec. 29, 1979 [DE] Fed. Rep. of Germany ....... 2952712

[51] Int. Cl.³ .................. G01N 23/00; G01J 1/00; G01N 21/84
[52] U.S. Cl. ........................ 250/359.1; 250/341; 356/430
[58] Field of Search ........... 250/339, 340, 341, 358 R, 250/359, 360, 562; 356/429, 430; 358/106, 113

[56] References Cited

U.S. PATENT DOCUMENTS

| | | | |
|---|---|---|---|
| 3,454,160 | 7/1969 | Schäfer | 250/562 |
| 4,118,732 | 10/1978 | Ichijima et al. | 358/113 |
| 4,302,108 | 11/1981 | Timson | 250/359 |
| 4,306,151 | 12/1981 | Chase | 250/359 |

Primary Examiner—Alfred E. Smith
Assistant Examiner—Janice A. Howell
Attorney, Agent, or Firm—Max Fogiel

[57] ABSTRACT

A device for detecting surface flaws of rapidly moving metal strip in rolling mills includes a lens which scans the sheet material surface and a camera tube which converts optical images of the lens into electrical values. These values are stored in a magnetic storage and are called out to be converted and displayed on an image reproducing device as a visible image. At least one image amplifier or image converter tube is interposed between the lens and the camera tube and includes an electronic speed shutter.

12 Claims, 5 Drawing Figures

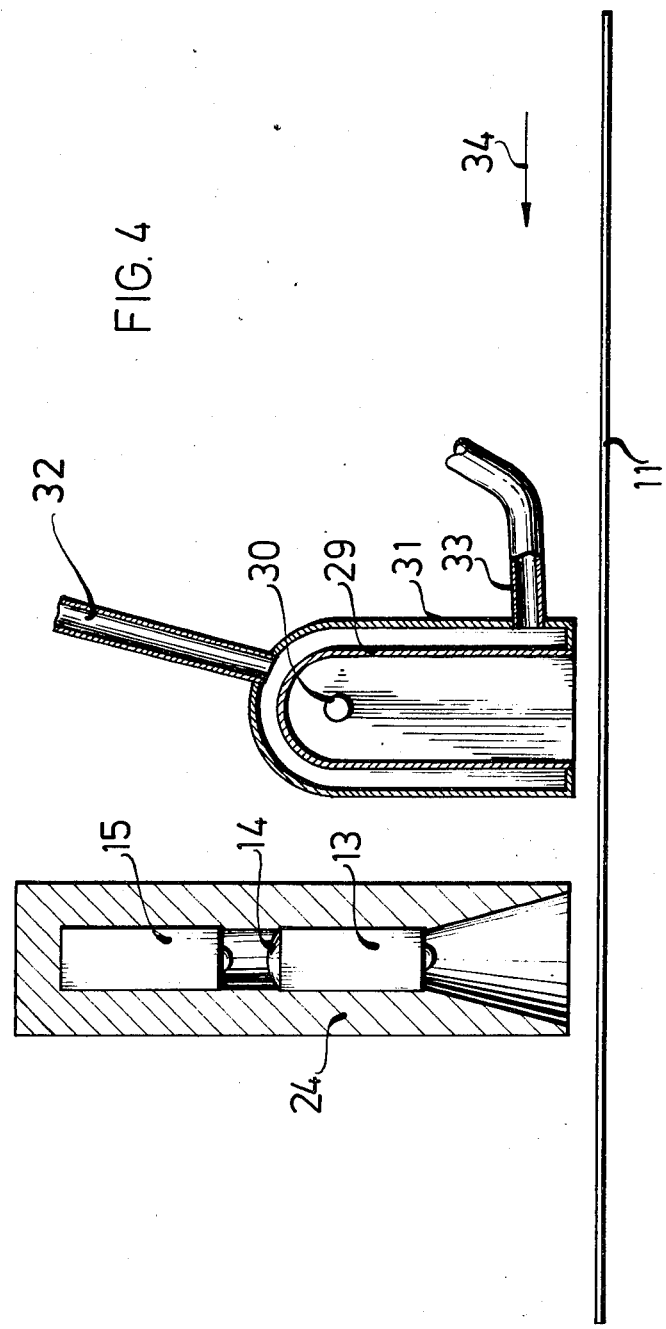

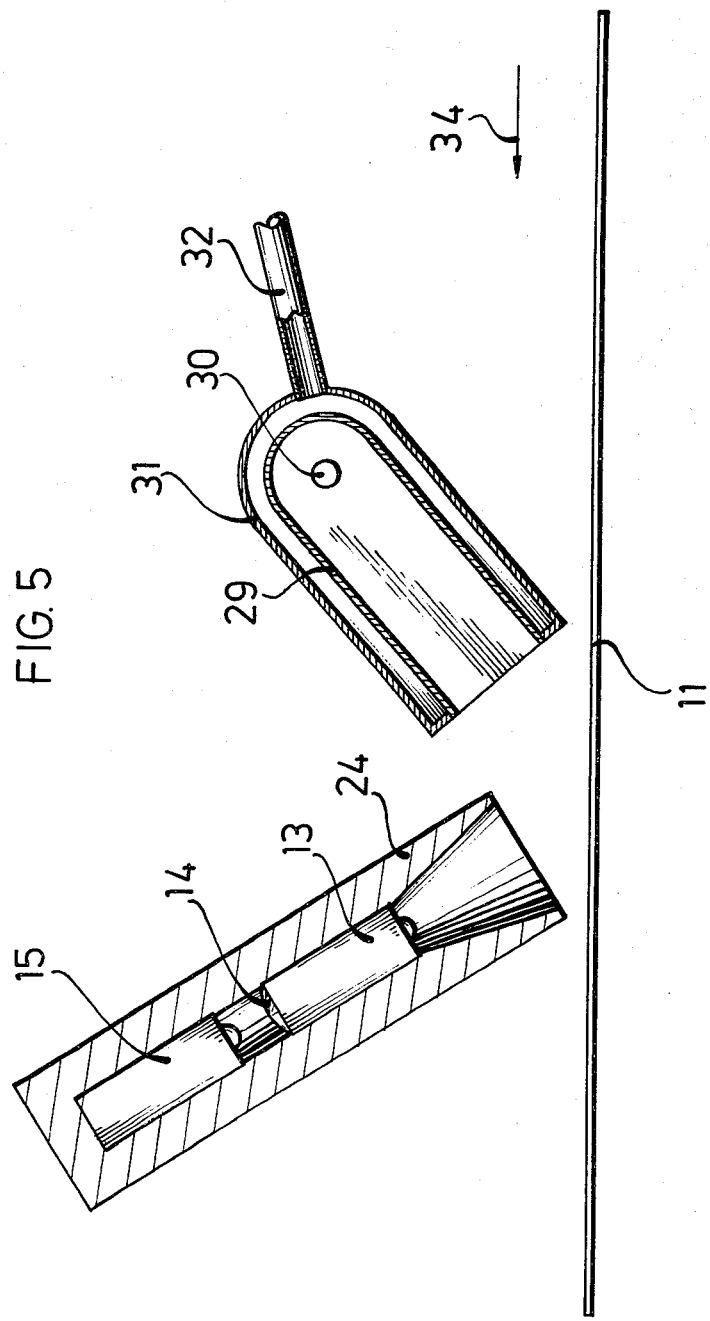

DEVICE FOR DETECTING SURFACE FLAWS OF RAPIDLY MOVING SHEET MATERIAL

BACKGROUND OF THE INVENTION

The present invention relates to a flaw detecting device, and more particularly to a device for detecting surface flaws of rapidly moving sheet material.

In particular, the invention relates to a device for detecting flaws on or in the surfaces of rapidly moving metal strip in rolling mills.

In modern rolling mills in which billets of metal are converted into sheet metal bands or tapes, the tapes move at speeds as high as 1600 meters per minute. At these speeds, it is very difficult to detect surface flaws in the strip material before the same is taken up to form strip material coils. Yet, the recognition of such flaws is important and it is therefore known, in order to make even relatively small flaws clearly visible, to illuminate the moving band with high-intensity stroboscopic lamps. These stroboscopic light flashes serve to produce a high intensity of light which increases the chance of identifying the flaws, and the short duration of the flashes eliminates the need for an optical speed shutter (rapidly operating shutter) which otherwise is necessary to obtain sharp-contour viewing when pictures are made of rapidly moving objects for direct observation by the naked eye or else by television or moving picture cameras.

The known devices have certain disadvantages. One of these is that a high flash sequence of at least 50 cycles is necessary, because lower flash sequences result in a flickering which has been found to be painful for even relatively far removed operating personnel. Moreover, the high flash frequency results in a rapid deterioration of the bulb and the high light intensity is found to be tiring to persons operating in the vicinity and may even cause damage to their eyes.

In addition, the use of monochromatic or polarized light for detecting flaws with the prior-art devices is impossible to all intents and purposes, because filters which would have to be placed in front of the flash lamps would filter out approximately 80% of the light and the residual light would yield only an insufficient light intensity. If, on the other hand, the output of the flash lamps is appropriately increased to overcome this problem and to restore the initial light intensity despite the use of the filters, then the currently common and already high output of 1000 Ws would be increased significantly by a multiple, and it would then be necessary to provide expensive cooling devices for the filters. Analogous disadvantages would result if the visible light would be replaced by light in the infrared or ultra-violet range.

SUMMARY OF THE INVENTION

It is, accordingly, an object of the present invention to avoid the disadvantages of the prior art.

A more particular object of the invention is to provide an improved device for detecting surface flaws of rapidly moving sheet material, particularly but not exclusively of metal strip in rolling mills.

Another object of the invention is to provide a device of the type in question which is capable of operating with a continuously visible mixed light having a substantially lower light intensity than heretofor necessary, but without thereby having to accept a reduction in the visibility of surface flaws.

A concomitant object is to provide a device of the type under discussion which can also be used to observe and identify surface flaws with the aid of monochromatic or polarized continuously visible light of low light intensity, and which can also be used for the same purpose while employing infrared or ultra-violet radiation that is invisible to the naked eye, in place of the visible light.

In keeping with these objects, and with still others which will become apparent hereafter, one feature of the invention resides in a device for detecting surface flaws of rapidly moving sheet material, particularly of metal strip in rolling mills. Briefly stated, such a device may comprise lens means for scanning the sheet material surface, and a camera tube for converting optical images received by the lens means into electrical values. A magnetic storage is connected with the camera tube to receive the electrical values therefrom and an image reproducing device is connected with the storage to receive the stored values and convert them into a visible image. At least one image amplifier or converter tube means is interposed between the lens means and the camera tube and includes an electronic speed shutter.

The invention will hereafter be described with reference to exemplary embodiments as illustrated in the appended drawings. It should be understood, however, that this is merely by way of explanation and that the parameters of the protection sought for the invention are exclusively defined in the claims hereof.

BRIEF DESCRIPTION OF THE DRAWINGS

FIG. 4 is a diagrammatic illustration, showing an infrared radiator with an infrared image converter located beyond it as considered in the direction of movement of the sheet material; and FIG. 5 is a diagrammatic illustration of an infrared image converter which receives reflected infrared radiation.

DESCRIPTION OF PREFERRED EMBODIMENTS

Figure 1:
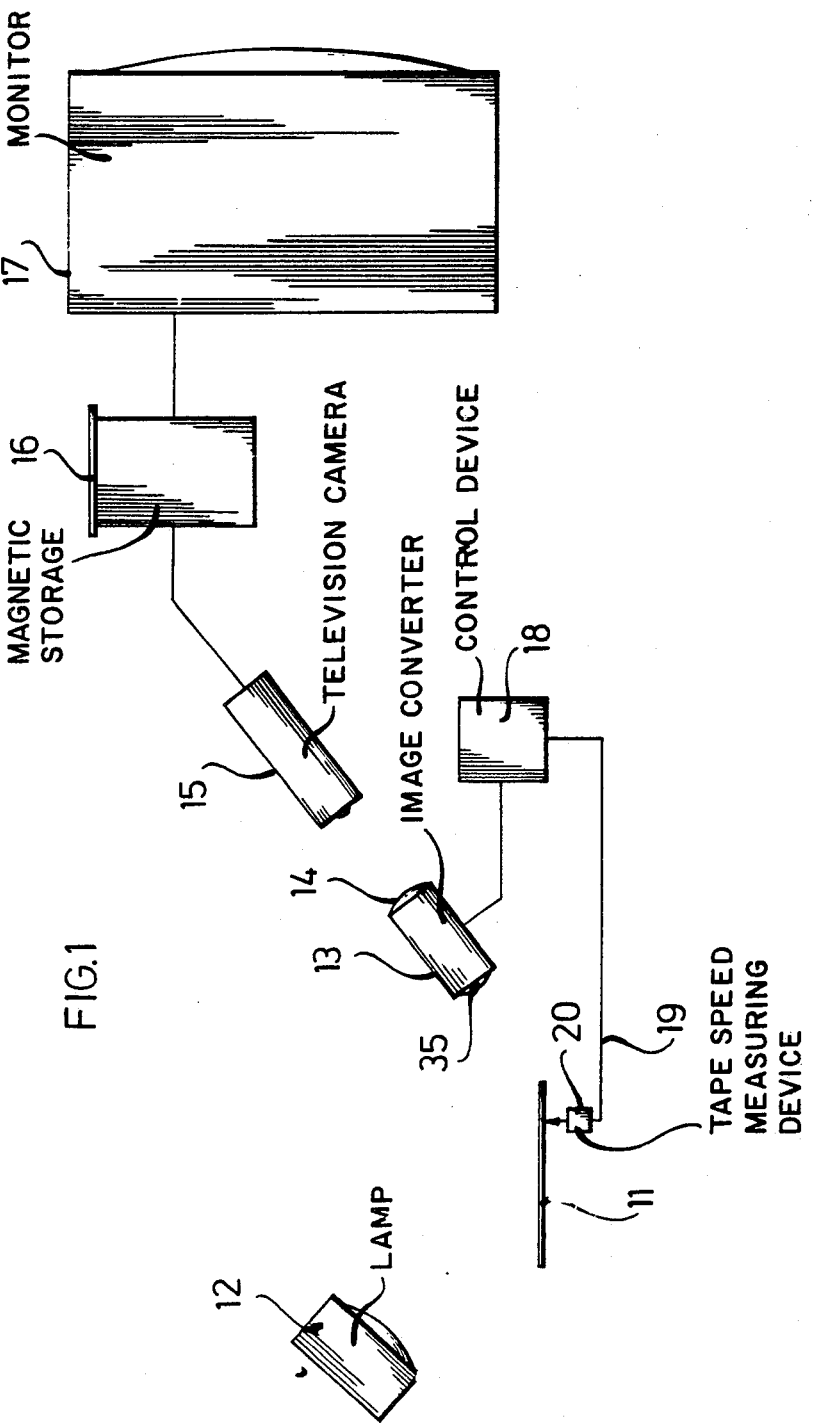
FIG. 1 is a diagrammatic illustration, showing an arrangement in accordance with the present invention which utilizes visible mixed light for illumination of the sheet material surface.

Referring firstly to FIG. 1 it will be seen that in this Figure the moving sheet material, for example a sheet material strip or tape of a rolling mill, is identified with reference numeral 11. A light source or lamp 11 directs illumination onto the surface of the sheet material 11. An image converter 13 having a lens is so adjusted that it receives a part of the reflection from the illuminated sheet material surface as an image, amplifies it and reproduces it on its viewing screen 14. A television camera 15 is directed against the viewing screen 14 and receives the image illustrated thereon, converting the image into electrical signals which are fed in a known manner into magnetic storages 16 where they are stored and from where they are sequentially called out for display on the monitor 17.

The image converting tube of the image converter 13 has a known blocking grid which, when charged by a negative voltage, interrupts the flow of the electrons to the viewing screen of the image amplifier. This blocking grid is normally negatively charge in blocking direction. By the use of known means, such as for example a trigger circuit, the blocking voltage is briefly negated for a period of 50 microseconds up to 1 millisecond. Only in this period of time can a picture be transmitted. Thus, the blocking grid acts like the speed shutter of a camera so that even very rapidly moving pictures can still be photographed and reproduced with sharp contours. The opening times are controlled by the speed of movement of the strip 11 itself. For this purpose the image converter 13 is connected with a control device 18 and a conductor 19 with a tape speed measuring device 20, in such a manner that when the speed of the tape or sheet material 11 increases, the opening time of the shutter, i.e. the time for which the blocking voltage of the grid is negated, is decreased. To increase the amplification further image amplifiers without blocking grids may be connected in circuit behind the first image amplifier 13.

Figure 2:
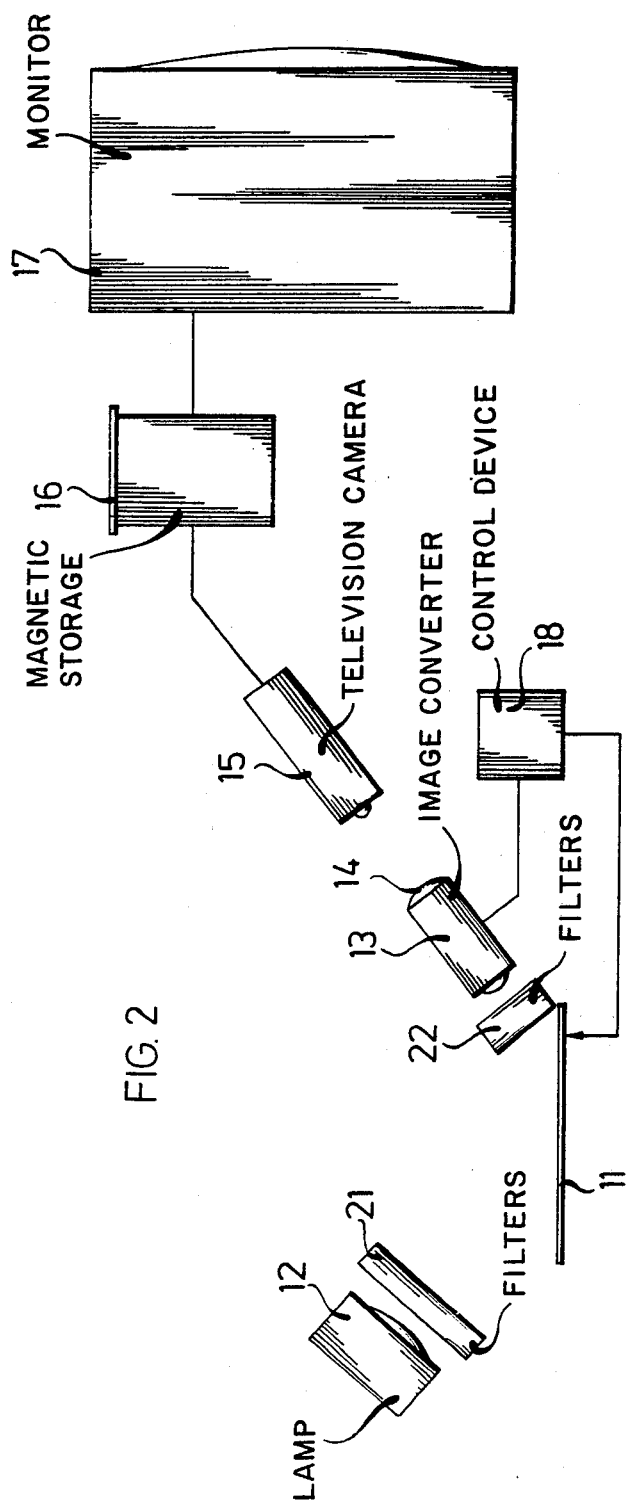
FIG. 2 is a view similar to FIG. 1, but of an arrangement capable of using monochromatic or polarized visible or ultra-violet invisible light.

Certain types of surface flaws on the sheet material 11 can be seen particularly clearly if the surface of the sheet material is illuminated with monochromatic or polarized light. In such an event (compare FIG. 2) appropriate filters 21 and 22 for the emission and receiving of these types of light are placed in front of the lamp 12 and in front of the lens of the image amplifier 13, as shown in FIG. 2. The lamp 12 can also be used to produce ultra-violet radiation if the image amplifier 13 is appropriately constructed to receive ultra-violet radiation.

Another possibility is to make the infrared radiation of the hot sheet material 11 itself visible, so as to thereby be enabled to identify surface flaws of the sheet material. If, for example, a particle or particles adhere to the roller or rollers used for rolling out the sheet material, and these particle or particles form small depressions in the surface of the sheet material 11, then the depression will be slightly warmer than the surrounding surface area immediately after the rolling, due to the shape change which took place when the depression was being formed. If an image amplifier is mounted above the sheet material 11 in the vicinity of the roller and is capable of receiving infrared radiation, then the depression will be visible on its screen as a bright heat radiation dot. The speed of the sheet material 11 is so high that the depression will already be past the infrared-receiving image amplifier before the heat from the depression can flow off and dissipate into the general vicinity.

Figure 3:
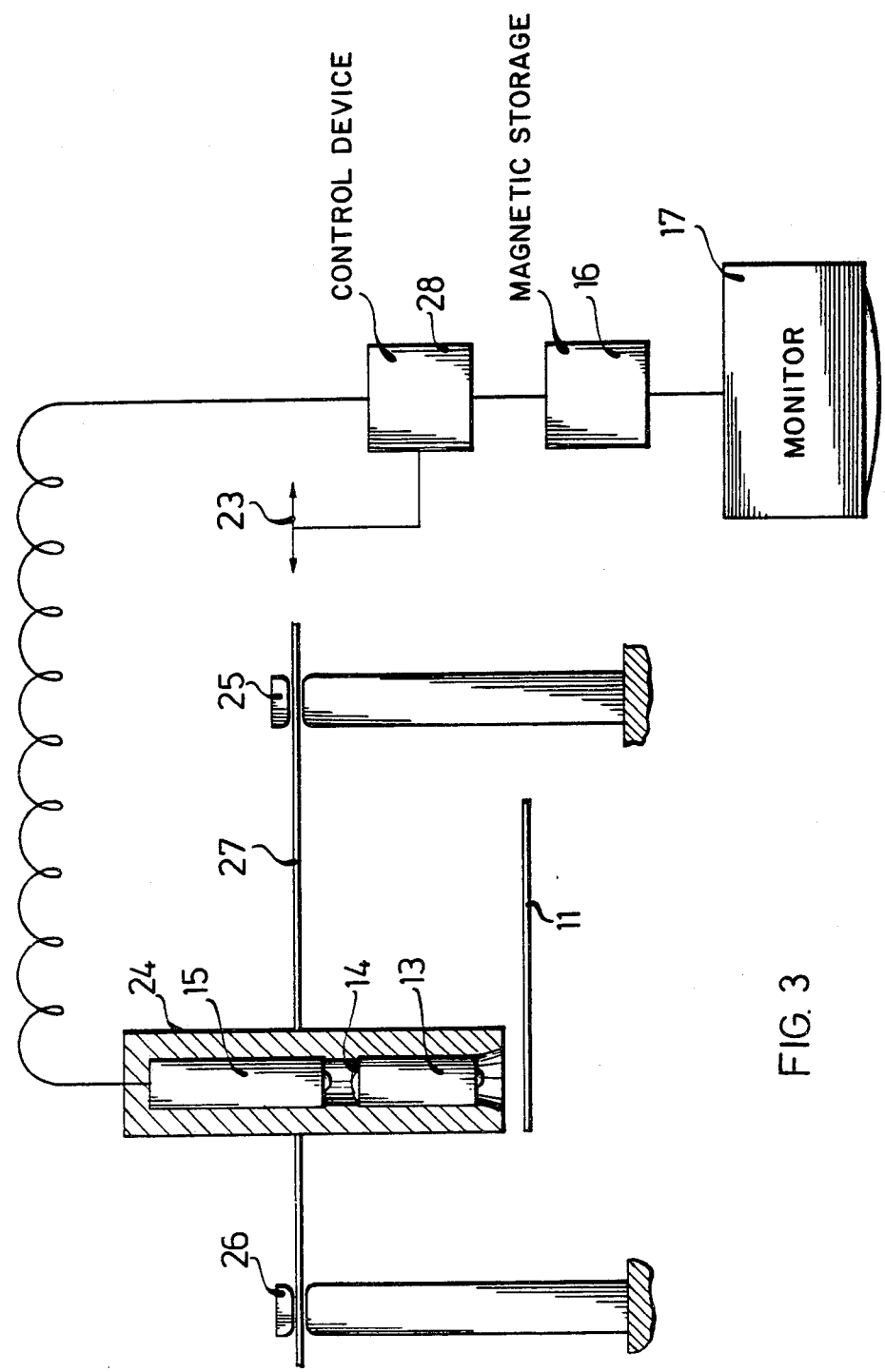
FIG. 3 is a view similar to FIG. 1 also, but illustrating an arrangement which utilizes infrared radiation.

Because the sheet material has substantially temperature fluctuations over its width, the scanning for surface flaws by means of infrared radiation can normally be carried out only over portions of the band or sheet material widths. However, the total width of the band or sheet material can be scanned and supervised with an arrangement as illustrated in FIG. 3, in which the image amplifier is mounted in a housing 24 which in turn is mounted on a rod 27 that is supported by the guides 25 and 26. An only diagrammatically illustrated drive 23 serves to shift the rods 27 lengthwise of itself, i.e. transversely to the width of the sheet material 11, and during this transverse movement several images are stored in the magnetic storage 16, which are brought up to a uniform average brightness by appropriate circuit in the control device 28. The individual stored images are jointly retrieved from the storage 16 by the control device 28, and are so displayed on the monitor 17 that an image of the total sheet material width is furnished.

As shown in FIG. 4, it is also possible to provide an arrangement in which the surface of the sheet material 11 is briefly heated by an infrared radiator which extends transversely across the sheet material 11. The infrared radiator is composed of a heating rod 30 which is mounted in a housing 29 that is metallic and reflective and open in the direction towards the sheet material 11. The housing 29 is surrounded with a small spacing by a second housing 31, and an air tube 32 and a not illustrated ventilator serve to draw air through the gap between the housings 29 and 31; this air is drawn upwardly and enters at the nipple 33. The infrared radiator serves particularly to heat dark, i.e. not metallically blank portions of the sheet material, which subsequently become visible on the screen of the image amplifier 13 as luminescent dots. The image amplifier 13 is mounted closely behind the infrared radiator, as considered in the direction of advancement 34 of the sheet material 11. This type of flaw detection is particularly well suited for coated sheet material and non-metallic materials.

Reflected infrared radiation may also be made visible on the screen of the image amplifier 13, if as shown in FIG. 5, the infrared radiator and the image amplifier are mounted so as to be inclined at an angle to one another.

It will be understood, of course, that it is certainly possible for a device according to the present invention to have several types of radiators for different types of radiation which can be individually or jointly operated, or to provide several types of radiators yielding different types of radiation and which are arranged one behind the other as considered in the direction of advancement 34 of the sheet material 11.

The invention has hereinbefore been described with reference to some exemplary embodiments. The invention sought for it, however, is defined exclusively in the appended claims.

What is claimed is:

1. Device for detecting surface flaws of rapidly moving sheet material, particularly of metal strip in rolling mills, comprising lens means for scanning the sheet material surface; a camera tube for converting optical images received by said lens means into electrical values; a magnetic storage connected with said camera tube to receive said electrical values therefrom; an image reproducing device connected with said storage to receive the stored values therefrom and convert them into a visible image; and at least one image amplifier tube means interposed between said lens means and camera tube and including an electronic speed shutter for interrupting plate voltage of said image amplifier tube means, said electronic speed shutter being built into said image amplifier tube means.

2. Device as defined in claim 1, said lens means and image amplifier tube means being of the type operable with visible-spectrum light for operation in conjunction with continuous illumination of the sheet material surface with an intensity of 3000–40000 lumen.

3. Device as defined in claim 1, said lens means and image amplifier tube means being of the type operable with infrared radiation.

4. Device as defined in claim 3; and further comprising means for directing infrared radiation at the sheet material surface.

5. Device as defined in claim 1; said lens means and image amplifier tube means being of the type operable with ultra-violet radiation.

6. Device as defined in claim 5; and further comprising means for directing ultra-violet radiation at the sheet material surface.

7. Device as defined in claim 1, the speed of advancement of the sheet material being measured by a speed measuring device; and wherein said electronic shutter is so coupled with the speed measuring device that the opening interval of the shutter decreases as the sheet material speed increases.

8. Device as defined in claim 1; further comprising means for illuminating the sheet material surface; and further means interposed between the illuminating means and the sheet material surface so that the surface is impinged by monochromatic light.

9. Device as defined in claim 1; further comprising means for illuminating the sheet material surface; and further means interposed between the illuminating means and the sheet material surface so that the surface is impinged by polarized light.

10. Device as defined in claim 1; further comprising at least two different alternatively activatable illuminating means each producing a different type of illuminating of the sheet material surface and each operable to illuminate the same surface portions as the other illuminating means.

11. Device as defined in claim 1; further comprising at least two different illuminating means each producing a different type of illumination for the sheet material surface and each operable to illuminate a sheet material surface portion different from but proximal to the surface portion being illuminated by the other illuminating means.

12. Device as defined in claim 1, said lens means and image converter tube means being of the type operable with visible-spectrum light for operation in conjunction with continuous illumination of the sheet material surface with an intensity of 3,000–40,000 lumen, the speed of advancement of the sheet material being measured by a speed measuring device, said electronic shutter being so coupled with said speed measuring device that the opening interval of the shutter decreases as the sheet material speed increases, means for illuminating the sheet material surface, and means interposed between the illuminating means and the sheet material surface so that the surface is impinged by monochromatic light.

* * * * *